United States Patent
Mori et al.

(10) Patent No.: US 12,249,072 B2
(45) Date of Patent: Mar. 11, 2025

(54) IMAGING DEVICE

(71) Applicant: PANASONIC HOLDINGS CORPORATION, Osaka (JP)

(72) Inventors: Toshihide Mori, Osaka (JP); Hirofumi Kanai, Osaka (JP); Yuka Yamada, Nara (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 19 days.

(21) Appl. No.: 17/991,486

(22) Filed: Nov. 21, 2022

(65) Prior Publication Data
US 2023/0085953 A1 Mar. 23, 2023

Related U.S. Application Data

(63) Continuation of application No. PCT/JP2021/001173, filed on Jan. 15, 2021.

(60) Provisional application No. 63/030,630, filed on May 27, 2020.

(30) Foreign Application Priority Data

Dec. 9, 2020 (JP) .................................. 2020-204230

(51) Int. Cl.
*G06T 7/00* (2017.01)
*G06T 7/80* (2017.01)

(52) U.S. Cl.
CPC .............. *G06T 7/0012* (2013.01); *G06T 7/80* (2017.01)

(58) Field of Classification Search
CPC ................................ G06T 7/0012; G06T 7/80
See application file for complete search history.

(56) References Cited

U.S. PATENT DOCUMENTS

| 9,828,755 B1 * | 11/2017 | Clements | .................. E03D 9/08 |
| 2018/0153414 A1 | 6/2018 | Hall et al. | |
| 2022/0213675 A1 * | 7/2022 | Kramer | .................. H04N 23/56 |

FOREIGN PATENT DOCUMENTS

| CN | 110578360 A | * 12/2019 |
| JP | 2017-137708 | 8/2017 |
| JP | 2018-126331 | 8/2018 |

OTHER PUBLICATIONS

International Search Report issued in International Pat. Appl. No. PCT/JP2021/001173, dated Mar. 23, 2021, along with an English translation thereof.

* cited by examiner

*Primary Examiner* — Rowina J Cattungal
(74) *Attorney, Agent, or Firm* — GREENBLUM & BERNSTEIN, P.L.C.

(57) ABSTRACT

An image capturing device which captures an image of excrement is provided at a toilet having a bowl and includes a sensor unit including an image capturing sensor. A view angle and an attachment position of the sensor unit are set so that a detection area presumed to receive dropping excrement in the bowl falls within a view field of the sensor unit.

10 Claims, 16 Drawing Sheets

IMAGING DEVICE

TECHNICAL FIELD

This disclosure relates to an image capturing device which captures an image of excrement.

BACKGROUND ART

Objective management of excrement for care receivers has been recently demanded in care facilities. For the management, technologies of attaching an image capturing device which captures an image of excrement to a toilet have been proposed. For instance, Patent Literature 1 discloses an excrement photographing apparatus including a plate part attached to a rearward upper surface of a bowl part, and photographing means at the plate part to face the bowl part and photograph an image of excrement.

However, in the technology of Patent Literature 1, the photographing means is fixed to face the bowl part. Therefore, the technology has difficulty in allowing dropping excrement in the bowl part to fall within a view angle of the photographing means, and thus needs further improvement.

CITATION LIST

Patent Literature 1: Japanese Unexamined Patent Publication No. 2018-126331

SUMMARY OF INVENTION

This disclosure has been achieved in view of the drawbacks described above, and has an object of providing an image capturing device to allow dropping excrement in a bowl to fall within a view angle thereof.

An image capturing device according to an aspect of the disclosure is an image capturing device that captures an image of excrement. The image capturing device includes a sensor unit attached to a fringe part of a toilet having a bowl, the fringe part being located at a top of the bowl, the sensor unit including an image capturing sensor. A view angle and an attachment position of the sensor unit are set so that a detection area presumed to receive dropping excrement in the bowl falls within a view field of the sensor unit.

According to the disclosure, the dropping excrement in the bowl is allowed to fall within the view angle.

DESCRIPTION OF EMBODIMENTS

Circumstances LED Up to this Disclosure

Figure 1:
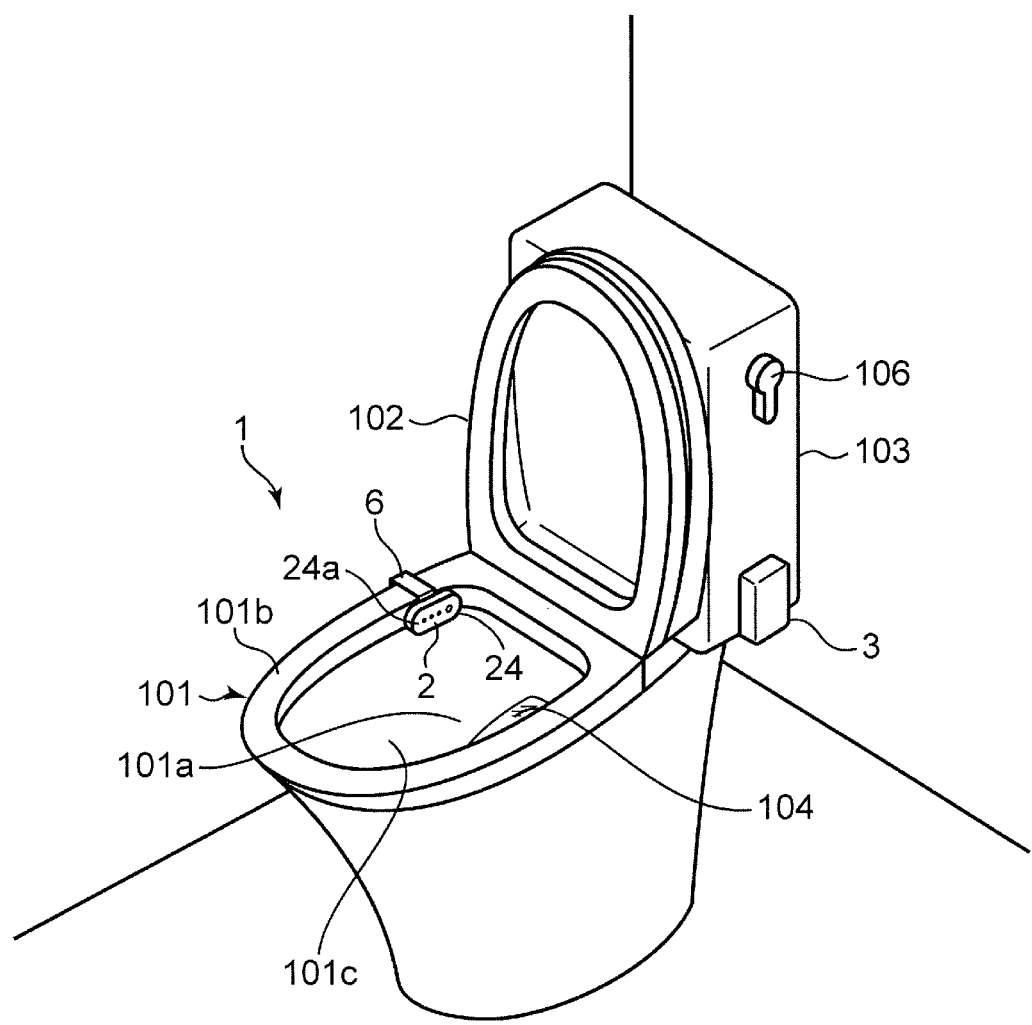
FIG. 1 is an external view of a toilet adopting an image capturing device according to a first embodiment of the disclosure.

Excretion history information indicating a frequency and a time of each excretion of defecation, urination, and flatulating is important to grasp a possible health risk of a person. In particular, a care facility accommodating many elderly people who tend to have constipation demands objective recordation of excretion history information about care receivers to cause each of the care receivers to appropriately take a medicine like a laxative. However, such a care facility accommodates a large number of care receivers. Hence, the recordation of the excretion history information by caregivers or careers results in increasing the burden on the caregivers, and thus is not easy for them. Under the circumstances, the present inventors have advanced their studies on the technology of automatically managing excretion history information without human labor.

For automatic generation of the excretion history information, it is effective to provide an image capturing device to a toilet to capture an image of dropping excrement in a bowl by the provided image capture device, and analyze and record thus obtained image data.

However, a typical image capturing device has a narrow view angle of 45 degrees. Setting of the typical image capturing device to the toilet may cause a case where dropping excrement in a bowl fails to fall within the view angle of the image capturing device. Besides, an image capturing device generally called a wide-angle camera has a view angle of 60 degrees. Even the image capturing device of this type faces difficulty in allowing the dropping excrement in the bowl to fall within the view angle. Arrangement of such a conventional image capturing device at a toilet accordingly results in a failure to accurately detect, based on the image data, existence of the excrement and a sort thereof.

An image capturing device having a super-wide angle may allow the dropping excrement in the bowl to fall within the view angle thereof. However, the view angle suitable for the dropping excrement in the bowl depends on an attachment position of the image capturing device. Hence, mere attachment of the image capturing device having the super-wide angle to the toilet may cause an excessive view angle or a lack of view angle.

Under the circumstances, the present inventors have obtained the knowledge that setting a view angle and an attachment position of a sensor unit so that at least a detection area presumed to receive dropping excrement in a bowl falls within the view field allows the dropping excrement in the bowl to fall within the view angle, and have conceived of the following aspects of the disclosure.

An image capturing device according to one aspect of the disclosure is an image capturing device that captures an image of excrement. The image capturing device includes a sensor unit attached to a fringe part of a toilet having a bowl, the fringe part being located at a top of the bowl, the sensor unit including an image capturing sensor. A view angle and an attachment position of the sensor unit are set so that a detection area presumed to receive dropping excrement in the bowl falls within a view field of the sensor unit.

According to this configuration, the view angle and the attachment position of the sensor unit are set so that at least the detection area of the sensor unit falls within the view field of the sensor unit, thereby allowing the excrement to fall within the view angle. As a result, existence of stool and a sort thereof is accurately detectable, based on the image data.

In the image capturing device, the fringe part may define an opening section. A center line of the opening section extending in a front-rear direction may bear, in a top view of the opening section, a first position being a predetermined position between a first intersection being a front intersection of the center line and the opening section and a second intersection being a front intersection of the center line and the detection area, and a second position being a predetermined position between a third intersection being a rear intersection of the center line and the detection area and a fourth intersection being a rear intersection of the center line and the opening section. The view angle and the attachment position of the sensor unit may be set so that the first position and the second position fall within the view field.

According to the configuration, the view angle and the attachment position of the sensor unit are set so that the first position and the second position fall within the view field. This reliably allows the excrement to fall within the view angle.

In the image capturing device, the first position may be at the first intersection, and the second position may be at the fourth intersection.

According to this configuration, the first position is at the first intersection being the front intersection of the center line and the opening section, and the second position is at the fourth intersection being the rear intersection of the center line and the opening section, which allows a large region of the bowl to fall within the view angle. This further reliably allows the excrement to fall within the view angle.

In the image capturing device, the attachment position may be in an oblique rear of the detection area, and the view angle may have 83 degrees or more.

An angle required to allow a large region of a bowl to fall within a view angle in the attachment of the sensor unit in an oblique rear of a detection area has been confirmed to be 83 degrees as a result of attachment of the sensor unit to various types of toilets. In this configuration, the view angle is set to 83 degrees or more. Therefore, attachment of the sensor unit in the oblique rear of the detection area allows the large region of the bowl to fall within the view angle thereof, resulting in further reliably allowing the excrement to fall within the view angle.

In addition, the toilet generally has a configuration where a toilet seat thereof extends toward an opening section in the oblique rear of the bowl when the toilet seat is laid on the bowl. In this configuration, attachment of the sensor unit in the oblique rear of the detection satisfactorily makes the sensor unit inconspicuous from a defecator.

In the image capturing device, the attachment position may be in front or in the rear of the detection area.

A view angle required to allow a large region of a bowl to fall within a view field in the attachment of the sensor unit in front or in the rear of the detection area has been confirmed to be 101 degrees as a result of attachment of the sensor unit to various types of toilets. In the configuration, the view angle is set to 101 degrees or more. Therefore, the attachment of the sensor unit in front or in the rear of the detection area allows the large region of the bowl to fall within the view angle thereof, resulting in further reliably allowing the excrement to fall within the view angle.

In the image capturing device, the view angle may have 105 degrees or more.

A view angle required to allow the large region of the bowl to fall within the view field regardless of the attachment position of the sensor unit has been confirmed to be 105 degrees as a result of attachment of the sensor unit to various types of toilets. In the configuration, the view angle is set to 105 degrees or more. Therefore, the large region of the bowl is allowed to fall within the view angle of the sensor unit regardless of the attachment position of the sensor unit. This further reliably allows the excrement to fall within the view angle.

The image capturing device may further include an attachment part for removably attaching the sensor unit to the toilet.

According to this configuration, the sensor unit is attachable to the toilet at any position thereof. Therefore, the sensor unit is retrofittable to an already-provided toilet.

The image capturing device may further include a calibration execution part that acquires, from the image capturing sensor, image data containing an image of a mark provided at a specific position of the toilet, detects an existent position of the mark from the acquired image data, and executes calibration of setting, based on the detected existent position, an area corresponding to the detection area to the image data.

According to this configuration, the existent position of the mark is detected from image data obtained by capturing an image of the mark, and executed is the calibration of setting, based on the detected existent position, an area corresponding to the detection area to the image data. The setting of the area corresponding to the detection area obtained through the calibration onto subsequently captured image data enables immediate extraction of an area including the excrement from the image data. As a result, existence of the excrement and a sort thereof is accurately and immediately determinable, based on the detection area. Moreover, storing not a whole of the image data but image data about the detection area as excretion history information in a memory leads to achievement of memory capacity saving. Furthermore, this configuration directed to image processing for the detection area succeeds in reducing a process burden more effectively than a configuration directed to processing for the whole of the image data.

The image capturing device may further include a gender determination part that detects a drop position of urine in the bowl from the image data captured by the image capturing sensor, and determining, based on the detected drop position, a gender of an excreter.

A drop position of urine in the bowl differs depending on a gender. According to this configuration, a drop position of urine in the bowl is detected from the image data, and a gender of an excreter is determined based on the drop position. This configuration enables specification of the gender of the excreter. This accordingly achieves generation of the excretion history information associating the gender with the image data.

In this configuration, the gender determination part may determine that the excreter is a male when the drop position falls within a first region, and determine that the excreter is a female when the drop position falls within a second region in the rear of the first region.

A drop position of urine in the bowl for a male is in front of that for a female. According to this configuration, the excreter is determined as a male when the drop position falls within the first region, and the excreter is determined as a female when the drop position falls within the second region in the rear of the first region. This configuration therefore achieves an accurate determination on the gender of the excreter.

In this configuration, the gender determination part may detect a sitting position of the excreter, and change, based on a determination result, the first region and the second region.

The drop position of urine differs depending on a sitting position regardless of an excreter of the same gender. According to this configuration, the first region and the second region are set based on a sitting position. This thus enables appropriate setting of the first region and the second region based on the sitting position, and further achieves an accurate determination on the gender of the excreter.

This disclosure can be further realized as: a program for causing a computer to execute each distinctive feature included in such an image capturing device; or a system operable by the program. Additionally, it goes without saying that the computer program is distributable as a non-transitory computer readable storage medium like a CD-ROM, or distributable via a communication network like the Internet.

Each of the embodiments which will be described below represents a specific example of the disclosure. Numeric values, shapes, constituent elements, steps, and the order of the steps described below are mere examples, and thus should not be construed to delimit the disclosure. Moreover, constituent elements which are not recited in the independent claims each showing the broadest concept among the constituent elements in the embodiments are described as selectable constituent elements. The respective contents are combinable with each other in all the embodiments.

First Embodiment

FIG. 1 is an external view of a toilet 101 adopting an image capturing device 1 according to a first embodiment. The toilet 101 is in the form of a toilet of a flush type. The toilet 101 includes a bowl 101a, a fringe part 101b, and an opening section 101c. The fringe part 101b is located at a top of the toilet 101 and has a frame shape to define the opening section 101c. The bowl 101a is located below the fringe part 101b and has a dome or bowl shape to receive stool and urine. The bowl 101a has a lower portion provided with a water pool part 104 therein. The water pool part 104 is deeply recessed downward to pool water. Pooled water in the water pool part 104 may exceed above an edge of the water pool part 104, but the excess of the pooled water above the edge of the water pool part 104 is not taken into consideration in the embodiment.

The water pool part 104 has a bottom provided with an unillustrated drain hole. The drain hole communicates with a sewage pipe to cause stool and urine excreted in the bowl 101a to flow to the sewage pipe.

Moreover, a toilet seat 102 is provided on the top of the toilet 101 to allow a user to sit thereon. The toilet seat 102 is attached to the toilet 101 rotatably about a rotary shaft provided to the fringe part 101b in a rear portion thereof. The user sits on the toilet seat 102 lowered to lie on the toilet 101. A water reservoir tank 103 that stores flush water to cause the stool and the urine excreted in the bowl 101a to flow is provided in the rear of the toilet 101.

A flush lever 106 is rotatably attached to a side wall of the water reservoir tank 103. When the flush lever 106 is rotated, the flush water in the water reservoir tank 103 is supplied into the bowl 101a to cause the stool and the urine excreted in the bowl 101a to flow to the sewage pipe via the drain hole.

The image capturing device 1 includes a sensor unit 2, a processing unit 3, and an attachment part 6. The attachment part 6 has one end to which the sensor unit 2 is attached for removably attaching the sensor unit 2 to the fringe part 101b. The attachment part 6 is made of material having pliability, e.g., resin, and fixedly attached to the fringe part 101b so as to sandwich the fringe part 101b thereover.

The sensor unit 2 includes a housing 24. The housing 24 accommodates therein an image capturing sensor 21 (see FIG. 9). The housing 24 has a main surface 24a formed with an opening section for guiding light to the image capturing sensor 21. The sensor unit 2 is attached to the fringe part 101b with the attachment part 6 so that the main surface 24a faces an inside of the fringe part 101b. The image capturing sensor 21 in the housing 24 thus can capture an image of a state of the bowl 101a.

The processing unit 3 is arranged, for example, on the side wall of the water reservoir tank 103. The processing unit 3 is communicably connected to the sensor unit 2 through a wireless or wired communication therebetween. The processing unit 3 acquires image data captured by the image capturing sensor 21, and determines, based on the acquired image data, whether or not stool is or defecation occurred.

Figure 2:
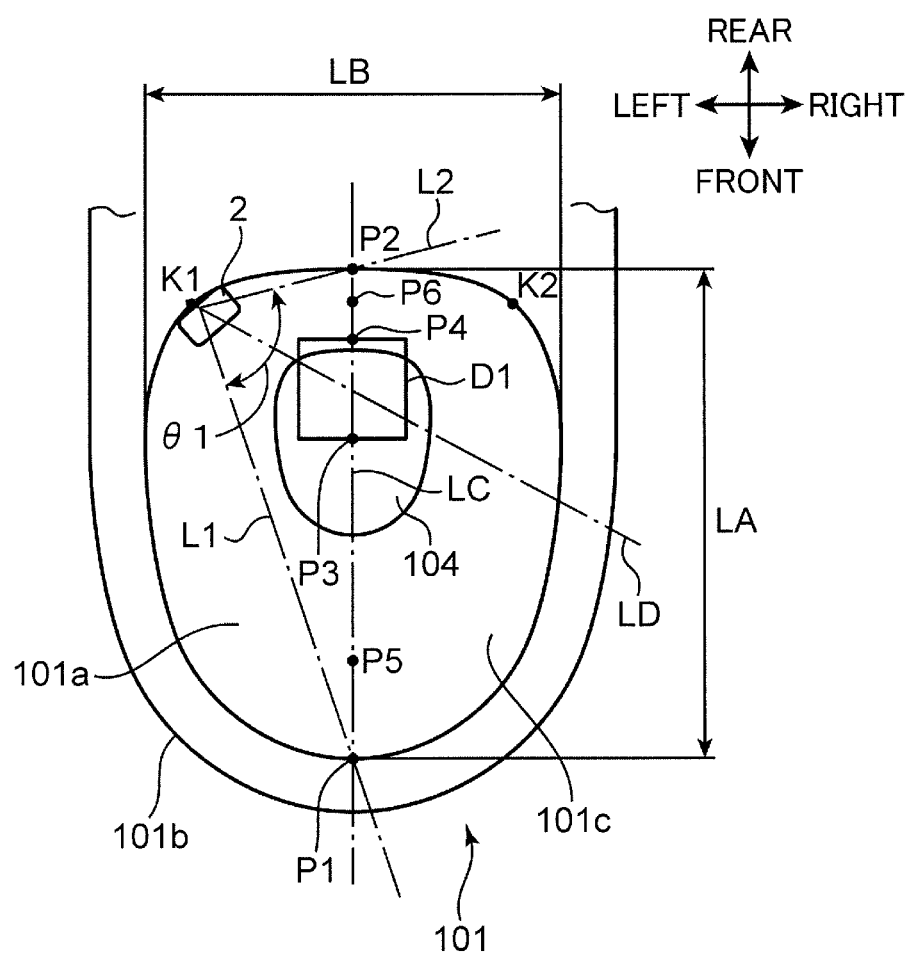
FIG. 2 shows an attachment example of a sensor unit shown in FIG. 1 to the toilet.

FIG. 2 shows an attachment example of the sensor unit 2 shown in FIG. 1 to the toilet 101. FIG. 2 shows the toilet 101 in a top view thereof. FIG. 2 omits illustration of the toilet seat 102. The omission is seen in FIGS. 3 to 8 as well.

The sensor unit 2 has a horizontal view angle of θ1. One of two boundaries defining the view angle θ1 is denoted by "L1" (first boundary) and the other is denoted by "L2" (second boundary). A region defined between the boundary L1 and the boundary L2 represents a view field of the sensor unit 2. A center line of the opening section 101c extending in the front-rear direction is denoted by "LC". Of two intersections of the opening section 101c and the center line LC, a front intersection is denoted by "P1" (first intersection) and a rear intersection is denoted by "P2" (fourth intersection). Of two intersections of the detection area D1 and the center line LC, a front intersection is denoted by "P3" (second intersection), and a rear intersection is denoted by "P4" (third intersection). A dimension of the opening section 101e in the front-rear direction is denoted by "LA", and a dimension thereof in the left-right direction is denoted by "LB". A center line of the view angle is denoted by "LD".

A contour of the opening section 101c has a substantially pentagonal shape with two inflection points K1, K2 in a rear portion thereof and three inflection points in a front portion thereof.

The sensor unit 2 may have a standard view angle of, for example, 45 degrees as its vertical view angle. Specifically, the sensor unit 2 is attached to the toilet 101 to be oblique downward by a half view angle (e.g., 22.5 degrees) of the standard view angle between a center line of the vertical view angle and the opening section 101e.

In the example shown in FIG. 2, the sensor unit 2 is attached in the oblique rear of the detection area D1. Specifically, the sensor unit 2 is attached at the left rear inflection point K1 on the contour of the opening section 101e. This is a mere example, and the sensor unit 2 may be attached at the right rear inflection point K2 on the contour of the opening section 101c.

The detection area D1 is presumed to receive dropping excrement (stool) in the bowl 101a and has, for example, a rectangular shape to overlap the water pool part 104 to a large extent.

At least the detection area D1 is required to fall within the view angle θ1 to capture an image of the dropping excrement in the bowl 101a. Preferably, a large region of the bowl 101a is required to fall within the view angle θ1. In the example shown in FIG. 2, the view angle θ1 is set so that the boundary L1 passes through the intersection P1 and the boundary L2 passes through the intersection P2.

In the attachment of the sensor unit 2 in the oblique rear of the detection area D1, a view angle θ1 required to cause the boundary L1 to pass through the intersection P1 and the boundary L2 to pass through the intersection P2 is measured. As a result, the required view angle θ1 is found to indicate about 83 degrees for a toilet 101 of a standard size with the dimension LA of 320 mm to 350 mm and the dimension LB of 290 mm. Specifically, the required view angle θ1 is found to indicate 83.4 degrees for a toilet 101 with the dimension LA of 350 mm. Therefore, in the example shown in FIG. 2, the view angle θ1 is set to 83.4 degrees. The view angle of the sensor unit 2 may be realized by adjusting a view angle of the image capturing sensor 21 or adjusting the opening section at the housing 24.

A toilet 101 of a large size has the dimension LA of 360 mm to 380 mm. In this case, the view angle θ1 is required to indicate about 87 degrees to cause the boundary L1 to pass through the intersection P1 and the boundary L2 to pass through the intersection P2. In this respect, in the attachment of the sensor unit 2 in the oblique rear of the detection area D1 in the toilet 101 of the large size, the view angle θ1 is set to about 87 degrees in the embodiment.

It is understood from these perspectives that the view angle θ1 may be set to 83.4 degrees or more, or to 83 degrees or more in consideration of a margin to cause the boundary L1 to pass through the intersection P1 and cause the boundary L2 to pass through the intersection P2 in the attachment of the sensor unit 2 in the oblique rear of the detection area D1 regardless of the standard size or large size.

The toilet seat 102 in a lying state on the fringe part 101b is likely to significantly extend toward the opening section 101c around the inflection points K1, K2 and is unlikely to extend toward the opening section 101c in a front portion of the fringe part 101b. Moreover, a periphery of the intersection P2 may be provided with a specific portion flusher, and therefore, is less suitable for the attachment of the sensor unit 2. In this regard, the attachment of the sensor unit 2 in the oblique rear of the detection area D1 is advantageous in facilitating the attachment of the sensor unit 2 and making the sensor unit 2 satisfactorily inconspicuous from an excreter.

Figure 3:
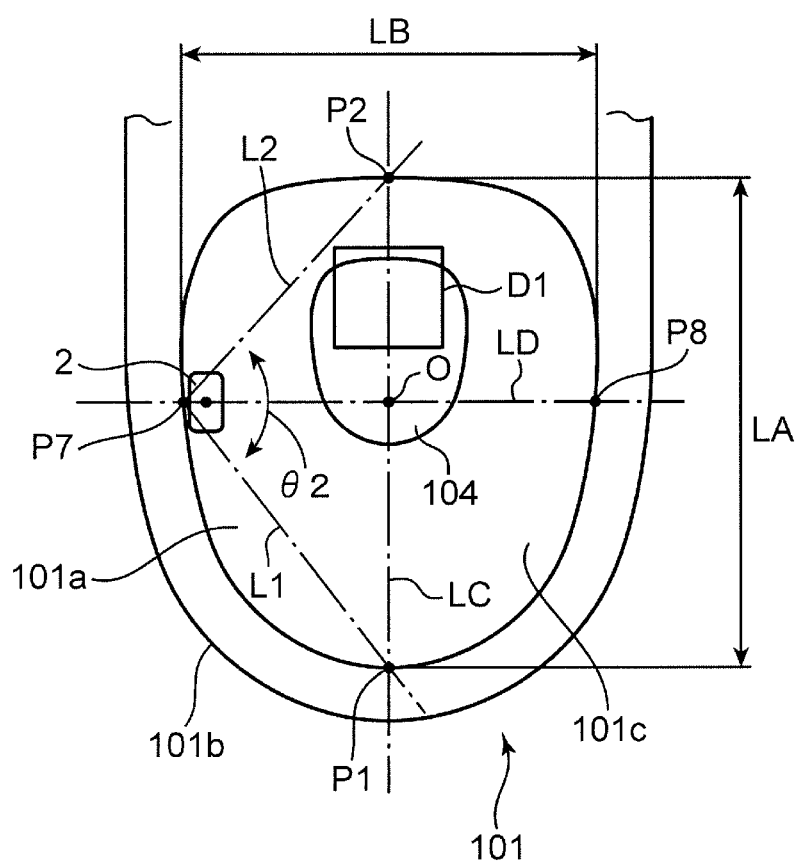
FIG. 3 shows another attachment example of the sensor unit shown in FIG. 1 to the toilet.

FIG. 3 shows another attachment example of the sensor unit 2 shown in FIG. 1 to the toilet 101. In the example shown in FIG. 3, the sensor unit 2 is provided on one side of the detection area D1. Specifically, the sensor unit 2 is attached at a left intersection P7 of the contour of the opening section 101c and a straight line passing through a center O of the opening section 101 and perpendicularly intersecting the center line LC. This is a mere example, and the sensor unit 2 may be attached at a right intersection P8. The center O is, for example, at the center of the center line LC.

In the attachment of the sensor unit 2 on the one side of the detection area D1, a view angle required to cause the boundary L1 to pass through the intersection P1 and the boundary L2 to pass through the intersection P2 is measured. As a result, the required view angle θ2 is found to be 101 degrees for the toilet 101 of the standard size. In contrast, the required view angle θ2 is found to be 105 degrees for the toilet 101 of the large size. Hence, in the arrangement of the sensor unit 2 on the one side of the detection area D1 in the embodiment, the view angle θ2 is set to 101 degrees for the toilet 101 of the standard size, and the view angle θ2 is set to 105 degrees for the toilet 101 of the large size.

Figure 4:
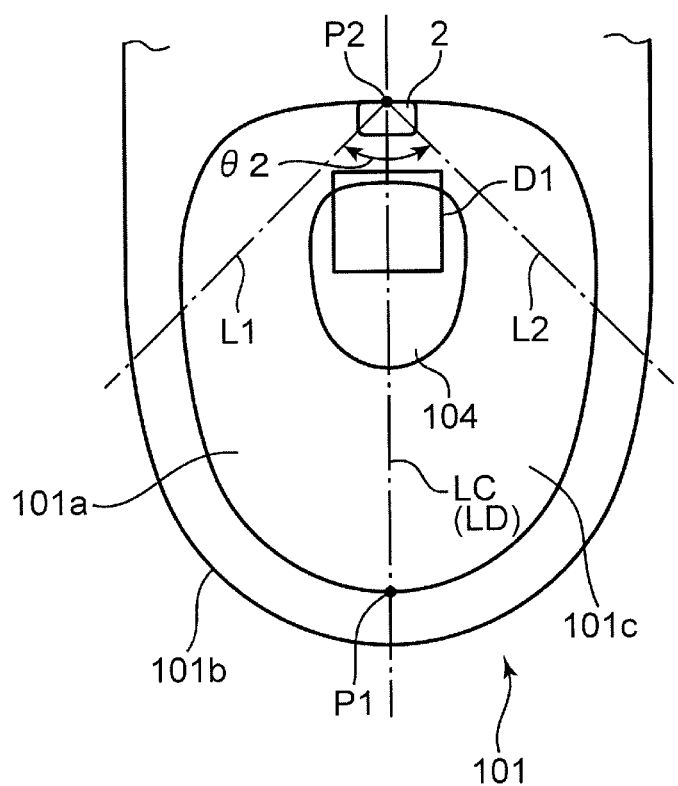
FIG. 4 shows further another attachment example of the sensor unit shown in FIG. 1 to the toilet.

FIG. 4 shows further another attachment example of the sensor unit 2 shown in FIG. 1 to the toilet 101. In the example shown in FIG. 4, the sensor unit 2 is provided in the rear of the detection area D1. Specifically, the sensor unit 2 is attached at the intersection P2. This is a mere example, and the sensor unit 2 may be attached at the intersection P1. In the example shown in FIG. 4, the view angle θ2 is set to the same value as that in FIG. 3. Specifically, the view angle θ2 is set to 101 degrees for the toilet 101 of the standard size, and the view angle θ2 is set to 105 degrees for the toilet 101 of the large size. This allows a large region of the bowl 101a to fall within the view angle θ2.

Figure 5:
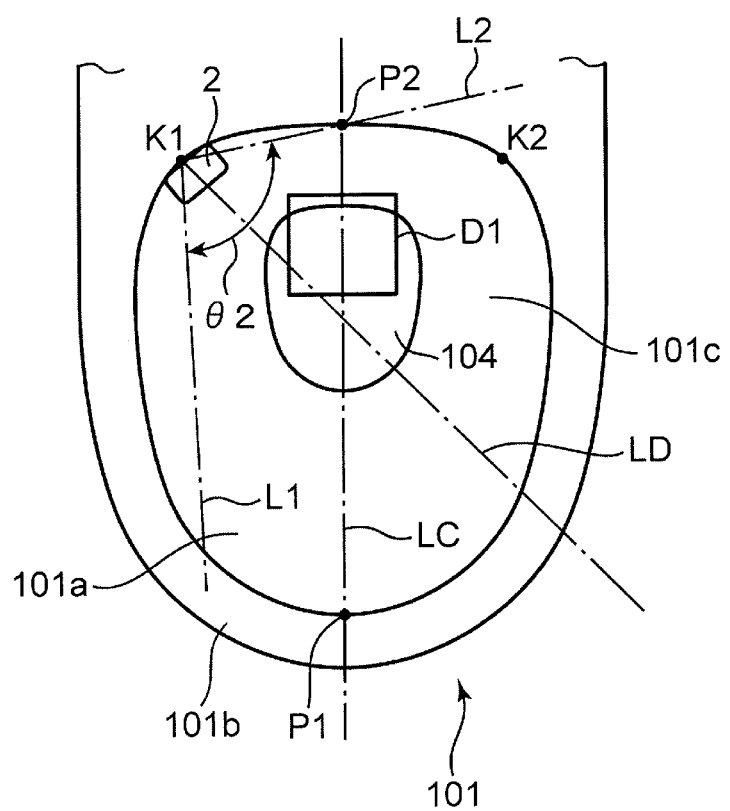
FIG. 5 shows still another attachment example of the sensor unit shown in FIG. 1 to the toilet.

FIG. 5 shows still another attachment example of the sensor unit 2 shown in FIG. 1 to the toilet 101. In the example shown in FIG. 5, the sensor unit 2 is attached to the toilet 101 of the standard size, and the view angle θ2 is set to 101 degrees. Besides, the sensor unit 2 is attached in the oblique rear of the detection area D1 in the same manner as the case shown in FIG. 2. In the example shown in FIG. 5, the view angle θ2 is set to 101 degrees, and therefore, the view angle θ2 contains the intersection P1 and the intersection P2.

It is seen from a change in the attachment position of the sensor unit 2 on the contour of the opening section 101c as shown in FIG. 2 to FIG. 5 that the view angle of the sensor unit 2 required to cause the boundary L1 to pass through the intersection P1 and cause the boundary L2 to pass through the intersection P2 takes a maximum value in the attachment of the sensor unit 2 on the one side of the detection area D1.

From these perspectives, a relation between an attachment position of the sensor unit 2 and a view angle of the sensor unit 2 is established in a manner to be described below.

Setting of the view angle of the sensor unit 2 to 105 degrees or more allows the position P1 and the position P2 to fall within the view angle in the toilet 101 of both the standard size and the large size regardless of the attachment position of the sensor unit 2.

Setting of the view angle of the sensor unit 2 to 101 degrees or more allows the position P1 and the position P2 to fall within the view angle in the toilet 101 of the standard size regardless of the attachment position of the sensor unit 2.

Setting of the view angle of the sensor unit 2 to 87 degrees or more allows the position P1 and the position P2 to fall within the view angle in the toilet 101 of both the large size and the standard size even in the attachment of the sensor unit 2 in the oblique rear of the detection area D1.

Setting of the view angle of the sensor unit 2 to 83 degrees or more allows the position P1 and the position P2 to fall within the view angle in the toilet 101 of the standard size even in the attachment of the sensor unit 2 in the oblique rear of the detection area D1.

Accordingly, the view angle of the sensor unit 2 takes a minimum value in the attachment of the sensor unit 2 in the oblique rear of the detection area D1.

Figure 6:
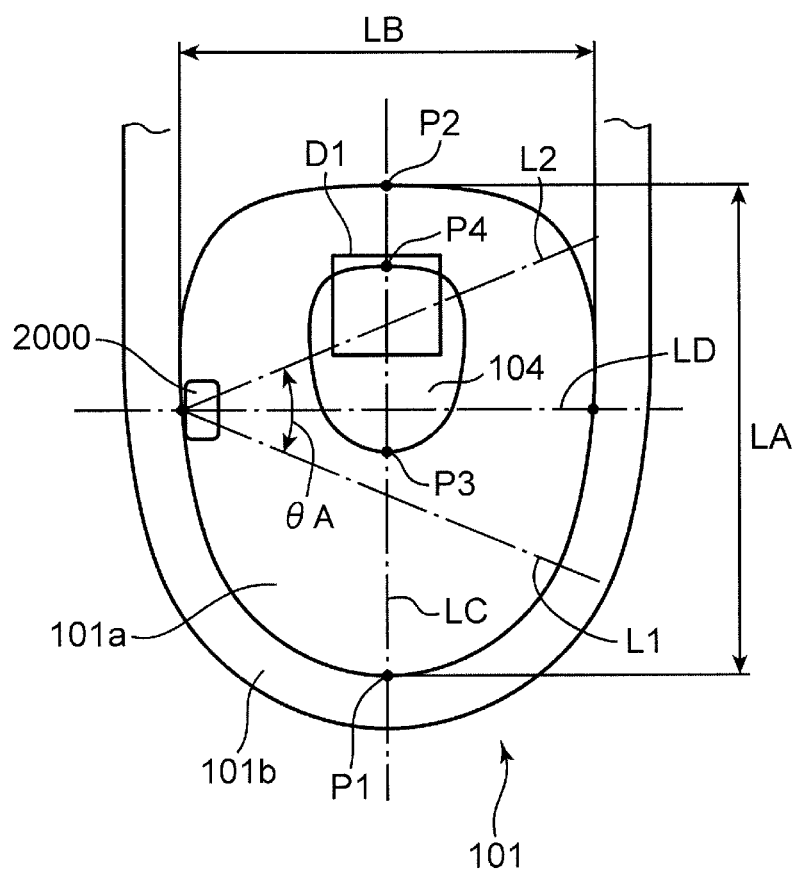
FIG. 6 shows an attachment example of a sensor unit in a comparative example of the disclosure to a toilet.

FIG. 6 shows an attachment example of a sensor unit 2000 in a comparative example of the disclosure to a toilet 101. The sensor unit 2000 adopts a standard angle of 45 degrees as a view angle θA. In the example shown in FIG. 6, the sensor unit 2000 is attached on one side of a detection area D1. The sensor unit 2000 has only the view angle θA of 45 degrees, and thus, an intersection P1 and an intersection P2 fail to fall within the view angle θA. Moreover, a boundary L2 is located in front of the intersection P4. Accordingly, the example shown in FIG. 6 fails to allow even the detection area D1, much less a large region of a bowl 101a, to fall within the view angle θA.

Figure 7:
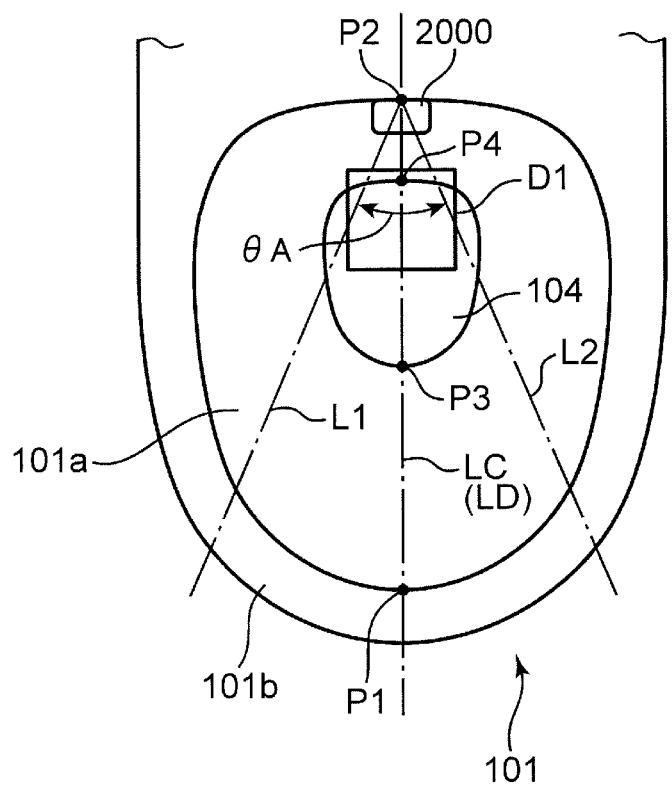
FIG. 7 shows another attachment example of the sensor unit in the comparative example of the disclosure to the toilet.

FIG. 7 shows another attachment example of the sensor unit 2000 in the comparative example of the disclosure to the toilet 101. In the example shown in FIG. 7, the sensor unit 2000 is attached in the rear of the detection area D1. The sensor unit 2000 has only the view angle θA of 45 degrees. Accordingly, the example shown in FIG. 7 fails to allow even the detection area D1, much less the large region of the bowl 101a, to fall within the view angle θA.

Figure 8:
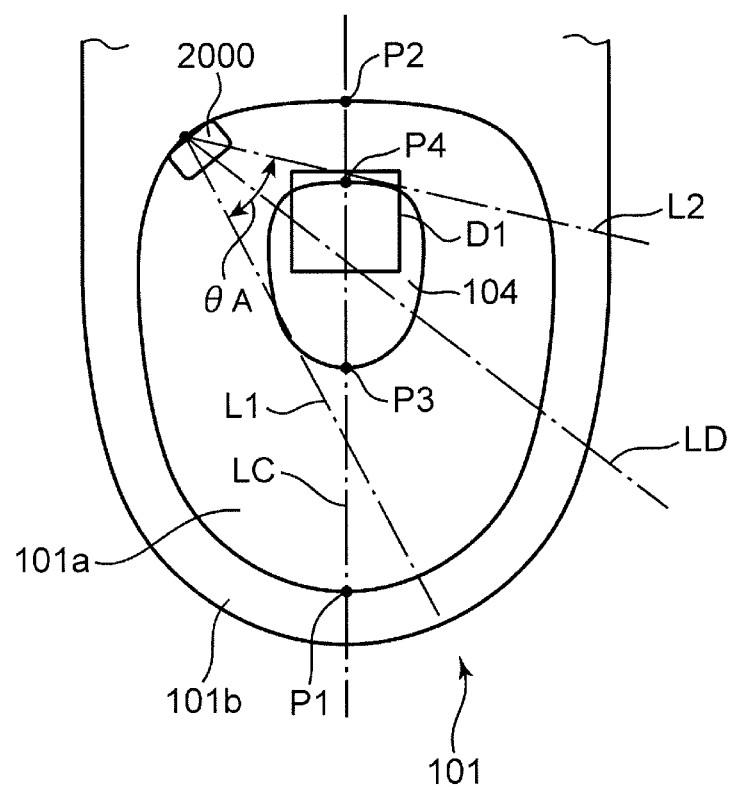
FIG. 8 shows further another attachment example of the sensor unit in the comparative example of the disclosure to the toilet.

FIG. 8 shows further another attachment example of the sensor unit 2000 in the comparative example of the disclosure to the toilet 101. In the example shown in FIG. 8, the sensor unit 2000 is attached in the oblique rear of the detection area D1. The sensor unit 2000 has only the view angle θA of 45 degrees. Hence, the boundary L2 passes through an inner position than the detection area D1, and therefore, even the detection area D1, much less the large region of the bowl 101a, fails to fall within the view angle θA.

Conclusively, the sensor unit 2000 in the comparative example fails to allow the detection area D1 to fall within the view angle θA. Therefore, it is highly unlikely to allow stool to fall within the view angle θA.

Figure 9:
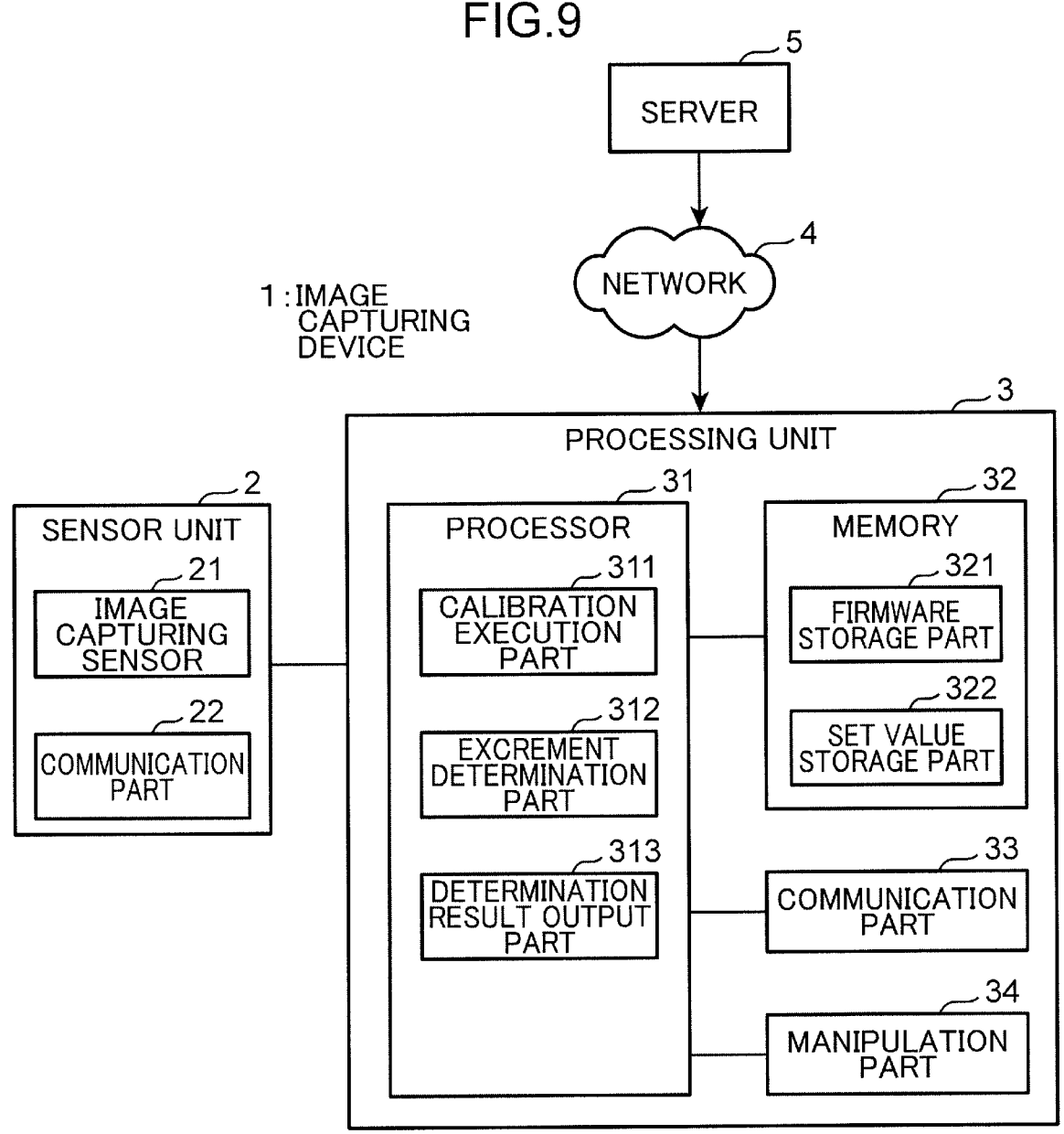
FIG. 9 is a block diagram showing an example of a configuration of the image capturing device according to the first embodiment of the disclosure.

FIG. 9 is a block diagram showing an example of a configuration of the image capturing device 1 according to the first embodiment of the disclosure. The image capturing device 1 includes the sensor unit 2 and the processing unit 3 each shown in FIG. 1. The sensor unit 2 includes the image capturing sensor 21 and a communication part 22.

The image capturing sensor 21 captures, for example, a color image having color components of R (red), G (green), and B (blue) at a predetermined frame rate. The communication part 22 includes, for example, a communication circuit for causing the sensor unit 2 to communicate with the processing unit 3 via a wireless or wired communication channel. The wireless communication channel includes a wireless LAN, such as the Wi-Fi (registered trademark). However, this is a mere example, and the wireless communication channel may include the Bluetooth (registered trademark) and infrared communication. The wired communication channel includes a wired LAN, such as IEEE 802.3. The communication part 22 transmits image data captured by the image capturing sensor 21 to the processing unit 3.

The processing unit 3 includes a processor 31, a memory 32, a communication part 33, and a manipulation part 34. The processor 31 includes an electric circuit, for example, a CPU, or an ASIC. The processor 31 includes a calibration execution part 311, an excrement determination part 312, and a determination result output part 313.

The calibration execution part 311 acquires, from the image capturing sensor 21, image data containing an image of a mark provided at a specific position of the toilet 101, detects an existent position of the mark from the acquired image data, and executes calibration of setting, based on the detected existent position, an area corresponding to the detection area D1 to the image data.

The detection area D1 is extracted from the image data as a target area for determining whether or not dropping excrement is in the bowl 101a and determining a sort thereof.

The excrement determination part 312 executes image processing based on the image data captured by the image capturing sensor 21 to determine whether or not excrement is in the bowl 101a and determine the sort thereof. Specifically, the excrement determination part 312 executes a process to be described below.

First, the excrement determination part 312 extracts from image data a detection area set through calibration, and calculates difference image data between image data of the extracted detection area and base image data.

The base image data is generated, for example, based on a plurality of pieces of image data of the bowl 101a as obtained by capturing images of the state of the bowl 101a without stool and urine by the image capturing sensor 21 a plurality of times. In other words, the base image data represents color image data of the detection area in a default state of the bowl 101a without stool and urine. Therefore, image data containing an image of stool, urine, or an unacceptable matter is extractable by taking a difference between the base image data and image data of the detection area captured at defecation or urination.

Subsequently, the excrement determination part 312 calculates an RGB ratio among each of the color components of R, G, B contained in the difference image data. The RGB ratio represents, for example, a ratio among a total value of the luminance of the R component, a total value of the luminance of the G component, and a total value of the luminance of the B component, in the difference image data.

Then, the excrement determination part 312 calculates a distance between the calculated RGB ratio and a predetermined stool RGB ratio, and determines that stool is in the bowl 101a when the calculated distance is equal to or shorter than a reference distance. The excrement determination part 312 further calculates a distance between the calculated RGB ratio and a predetermined urine RGB ratio, and determines that urine is in the bowl 101a when the calculated distance is equal to or shorter than the reference distance. Moreover, the excrement determination part 312 determines that an unacceptable matter is in the bowl 101a except for these cases. The unacceptable matter includes, for example, a paper diaper.

The determination result output part 313 generates, based on a detection result by the excrement determination part 312, excretion history information, and transmits the generated excretion history information to the server 5 via the communication part 33. The excretion history information associates information about excretion representing defecation or urination with daily time information about a date and time when the excretion occurred. Moreover, the excretion history information may include image data used for detection of excrement. In this case, the excretion history information may include only the region of the detection area D1 set in the image data.

The memory 32 includes a storage device, such as a flash memory. The memory 32 includes a firmware storage part

321 which stores firmware of the processing unit 3 and a set value storage part 322 which stores a set value of the detection area D1.

The communication part 33 includes a communication circuit having operability of communicably connecting the processing unit 3 to the sensor unit 2. The communication part 33 further includes operability of connecting the processing unit 3 to a network 4. The network 4 includes, for example, the internet. The communication part 33 transmits excretion history information to the server 5.

The manipulation part 34 includes one or more buttons, and receives inputs of various manipulations from a user.

Figure 10:
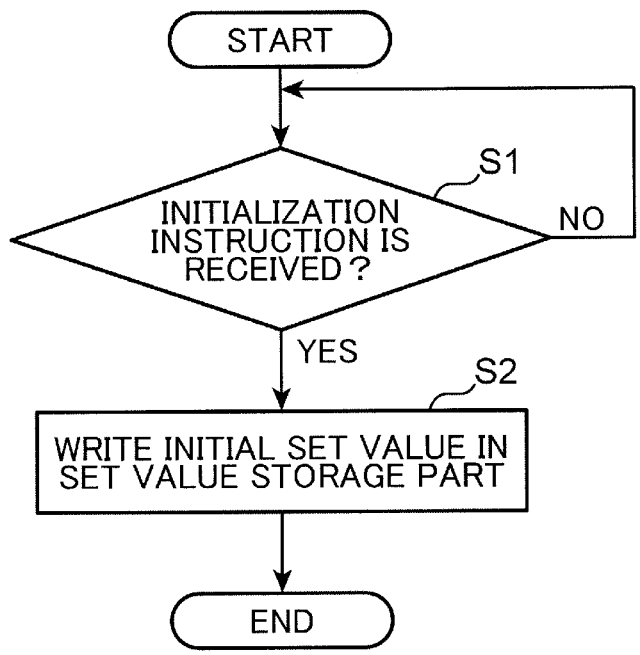
FIG. 10 is a flowchart showing an example of initialization of a set value in the first embodiment of the disclosure.

Next, the calibration will be described. Concerning the calibration, initialization of a set value and setting of the detection area are executed. FIG. 10 is a flowchart showing an example of initialization of a set value in the first embodiment of the disclosure.

The initialization of the set value is executed prior to the setting of the detection area. In step S1, the calibration execution part 311 determines whether the manipulation part 34 receives a predetermined manipulation to start the initialization. When the manipulation part 34 receives the predetermined manipulation (YES in step S1), the process proceeds to step S2. Contrarily, when the manipulation part 34 does not receive the predetermined manipulation (NO in step S1), the process waits in step S1.

In step S2, the calibration execution part 311 writes, in the set value storage part 322, an initial set value of the detection area D1 stored in the firmware storage part 321 as a set value of the detection area D1.

Figure 11:
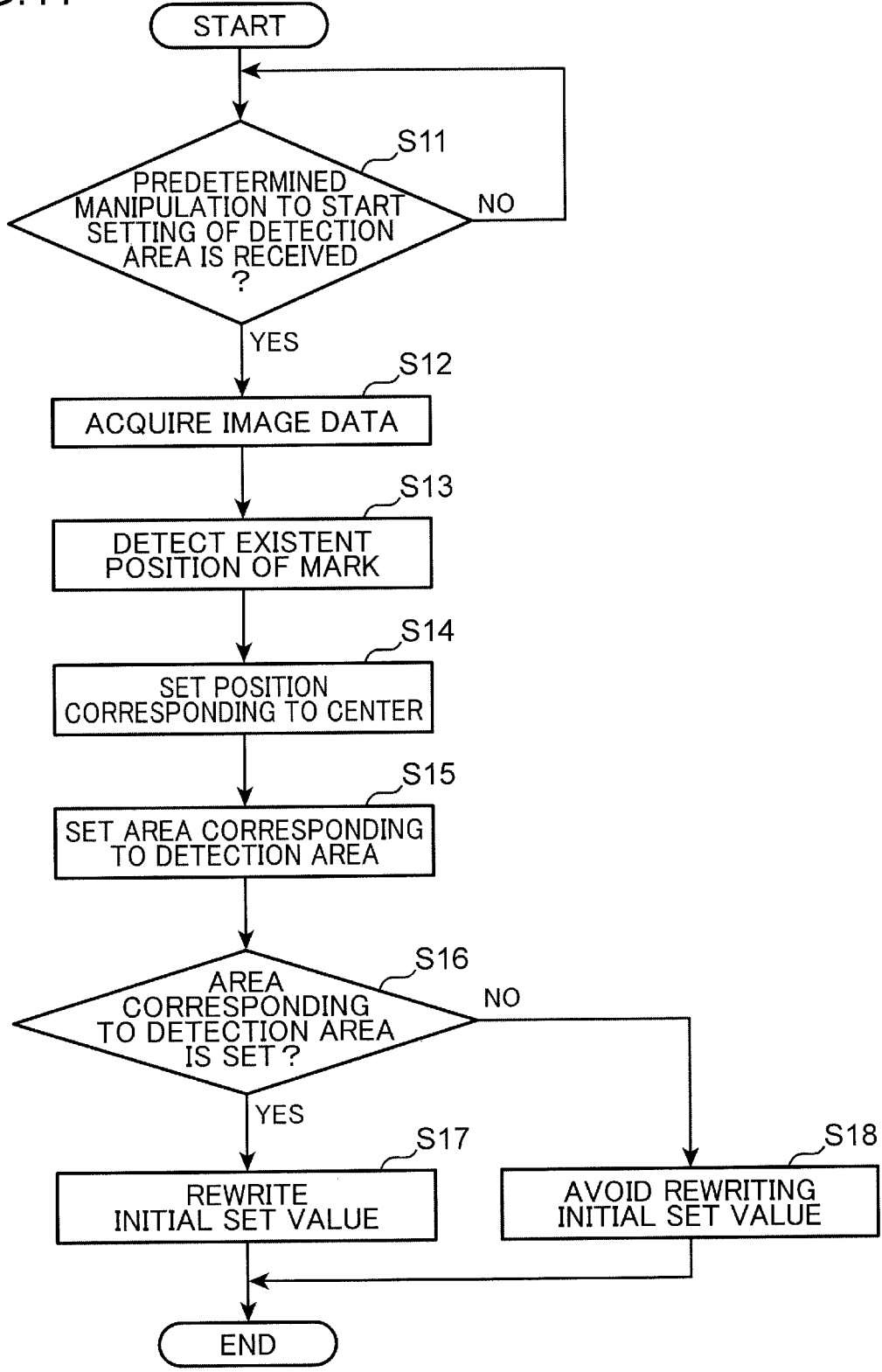
FIG. 11 is a flowchart showing an example of setting of a detection area in the first embodiment of the disclosure.

FIG. 11 is a flowchart showing an example of setting of the detection area D1 in the first embodiment of the disclosure. In step S11, the calibration execution part 311 determines whether the manipulation part 34 receives a predetermined manipulation to start the setting of the detection area D1.

When the predetermined manipulation is received (YES in step S11), the process proceeds to step S12. When the predetermined manipulation is not received (NO in step S11), the process waits in step S11. Examples of the predetermined manipulation to start the setting of the detection area D1 include a manipulation of pushing a predetermined button provided at a housing of the processing unit 3 for a while (e.g., for five seconds or longer).

In step S12, the calibration execution part 311 acquires image data from the image capturing sensor 21.

Figure 12:
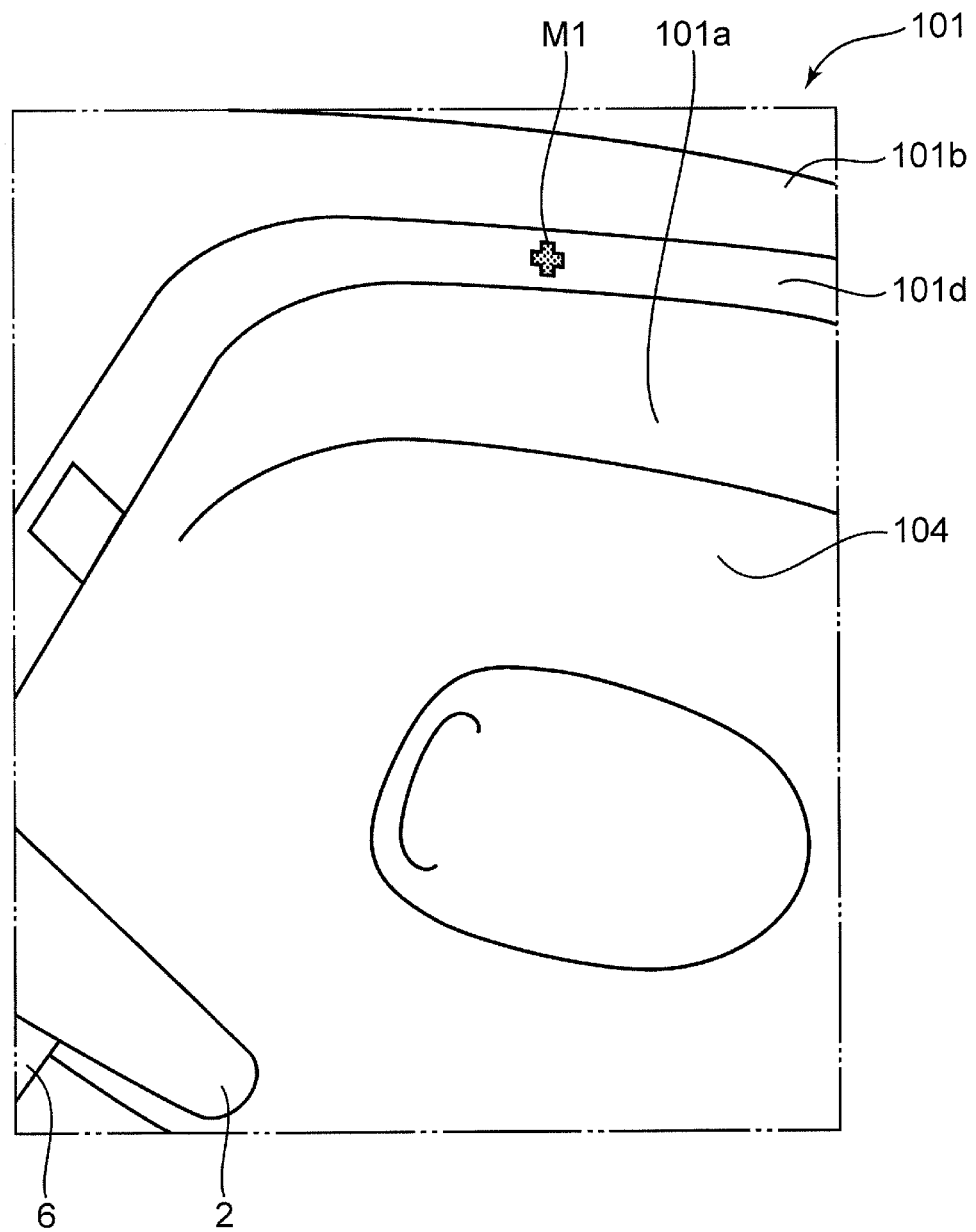
FIG. 12 shows a mark provided at the toilet.

In step S13, the calibration execution part 311 detects an existent position of a mark M1 on the image data, the mark being provided at a specific position of the toilet 101. The calibration execution part 311 may detect the existent position by using, for example, pattern recognition. FIG. 12 shows the mark M1 provided at the toilet 101. The mark M1 is formed of a seal, and is adhered to an inner wall 101d of the fringe part 101b of the toilet 101 by the user prior to the calibration. Specifically, the mark M1 is adhered to the inner wall 101d at the attachment of the sensor unit 2 to the toilet 101. The user to perform these works may be an end user or an operator who arranges the sensor unit 2.

Figure 13:
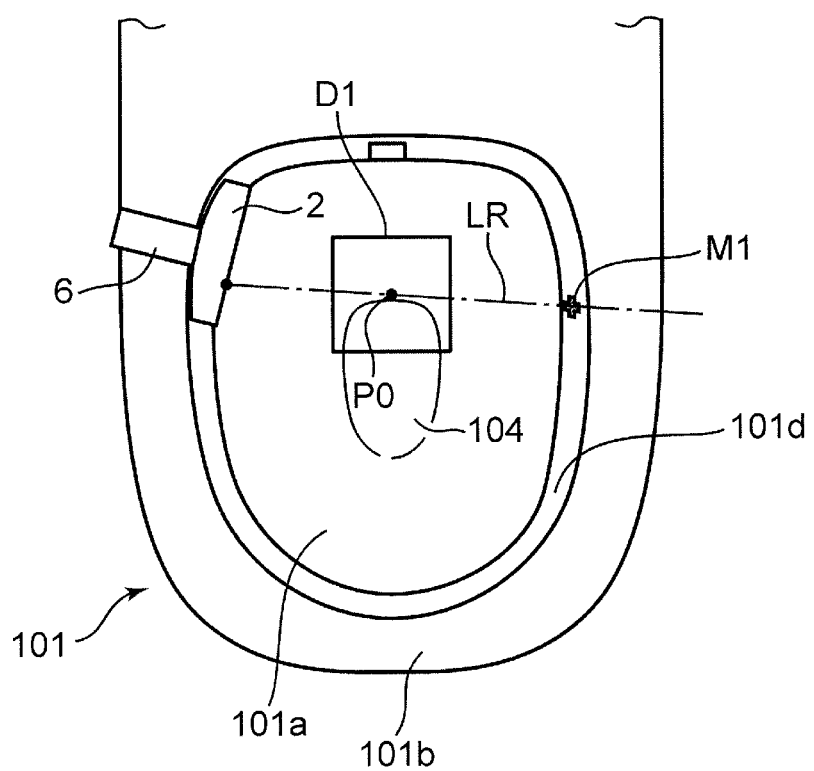
FIG. 13 is a view explaining an attachment work of the sensor unit.

FIG. 13 is a view explaining an attachment work of the sensor unit 2. First, the user attaches the attachment part 6 to the fringe part 101b and attaches the sensor unit 2 to the toilet 101 to avoid contact between a protrusion (not shown) located on a bottom surface of the toilet seat 102 and the fringe part 101b.

Next, the user presumes the detection area D1 in the bowl 101a. The detection area D1 is presumed to receive dropping stool. For instance, the detection area D1 is defined to have a center P0 located at a rear end of the water pool part 104 or in the vicinity of the rear end, and have a size equivalent to the size of the water pool part 104. However, this is a mere example, and the size of the detection area D1 may be larger or smaller than the size of the water pool part 104. The user may presume the detection area D1 by referring to, for example, a detection area D1 shown in an instruction manual of the sensor unit 2.

Subsequently, the user adheres the mark M1 at an intersection of the inner wall 101d and a reference line LR passing between the center P0 of the detection area D1 and the opening section provided at the housing 24 of the sensor unit 2 for guiding light to the image capturing sensor 21. As shown in FIG. 12, the mark M1 has, for example, a cross shape. The user adheres the mark M1 so that a vertical section of the mark M1 having the cross shape faces in a vertical direction and a horizontal section of the mark faces in a horizontal direction.

In step S14, the calibration execution part 311 sets, on the image data, a position corresponding to the center P0 of the detection area D1 at a predetermined distance from the existent position of the mark M1 in a specific direction. For instance, the calibration execution part 311 may set the position corresponding to the center P0 on a line extending from a lower end of the vertical section of the mark M1 having the cross shape to exist on the image data at a predetermined distance from the mark. The predetermined distance may take, for example, a value set in advance, based on a distance of a presumed line segment corresponding to a line segment from the mark M1 to the center P0 as projected onto an image capturing plane of the image capturing sensor 21.

In step S15, the calibration execution part 311 sets an area corresponding to the detection area D1 on the image data with reference to the position corresponding to the center P0. Each of the shape and size of the area corresponding to the detection area D1 takes a value set in advance based on the size and shape of a detection area D1 presumed when the detection area D1 is projected onto the image capturing plane of the image capturing sensor 21.

In step S16, the calibration execution part 311 determines whether the area corresponding to the detection area D1 is set. When the area corresponding to the detection area D1 is set (YES in step S16), the calibration execution part 311 rewrites an initial set value stored in the set value storage part 322 to a set value of the area corresponding to the detection area D1 (step S17). Examples of the set value of the area corresponding to the detection area D1 include a coordinate indicating the shape of the area corresponding to the detection area D1. Contrarily, when the area corresponding to the detection area D1 is not set (NO in step S16), the calibration execution part 311 avoids rewriting the initial set value (step S18). Consequently, the calibration is finished. Examples of where the area corresponding to the detection area D1 is not set include a case where the mark M1 is not detectable, a case where a position corresponding to the center P0 is not settable on the image data, and a case where the area corresponding to the detection area D1 does not fall within the image data.

Conclusively, in the image capturing device 1 according to the first embodiment, the attachment position and the view angle of the sensor unit 2 are set as described above, and therefore, a large region of the bowl 101a as well as the detection area D1 is allowed to fall within the view angle of the sensor unit 2.

Second Embodiment

A second embodiment aims at making a determination, based on a drop position of urine, on a gender of an excreter.

Figure 14:
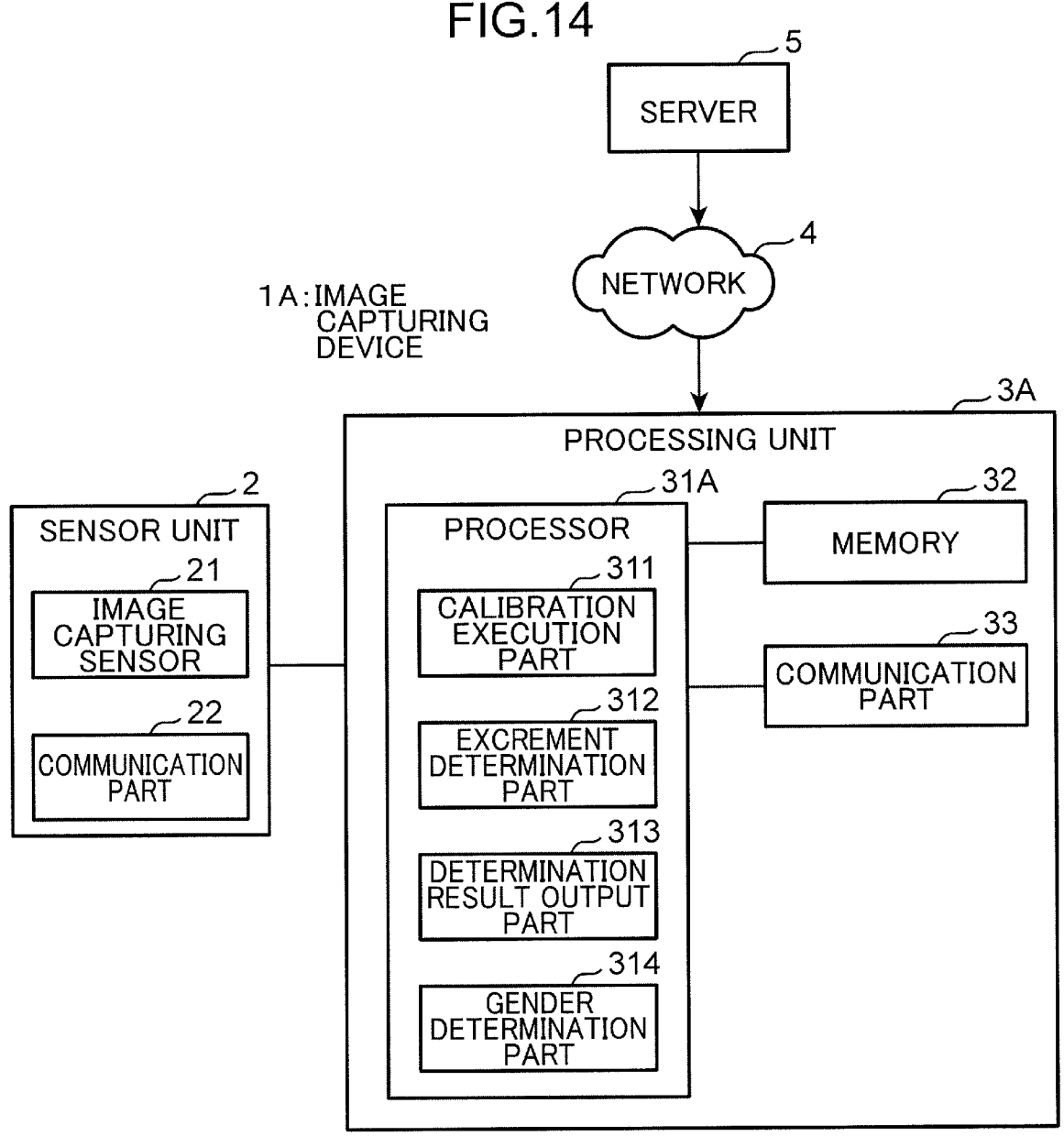
FIG. 14 is a block diagram showing an example of a configuration of an image capturing device according to a second embodiment of the disclosure.

FIG. 14 is a block diagram showing an example of a configuration of an image capturing device A1 according to the second embodiment of the disclosure.

A processor 31A included in a processing unit 3A of the image capturing device 1A further includes a gender determination part 314 in comparison with the processor 31 shown in FIG. 9.

The gender determination part 314 detects a drop position of urine in a bowl 101a from image data captured by an image capturing sensor 21, and determines, based on the detected drop position, a gender of an excreter.

Here, the gender determination part 314 may determine that the excreter is a male when the detected drop position falls within a first region, and may determine that the excreter is a female when the drop position falls within a second region in the rear of the first region.

Moreover, the gender determination part 314 may detect a sitting position of the excreter, and changes, based on a determination result, the first region and the second region.

Figure 15:
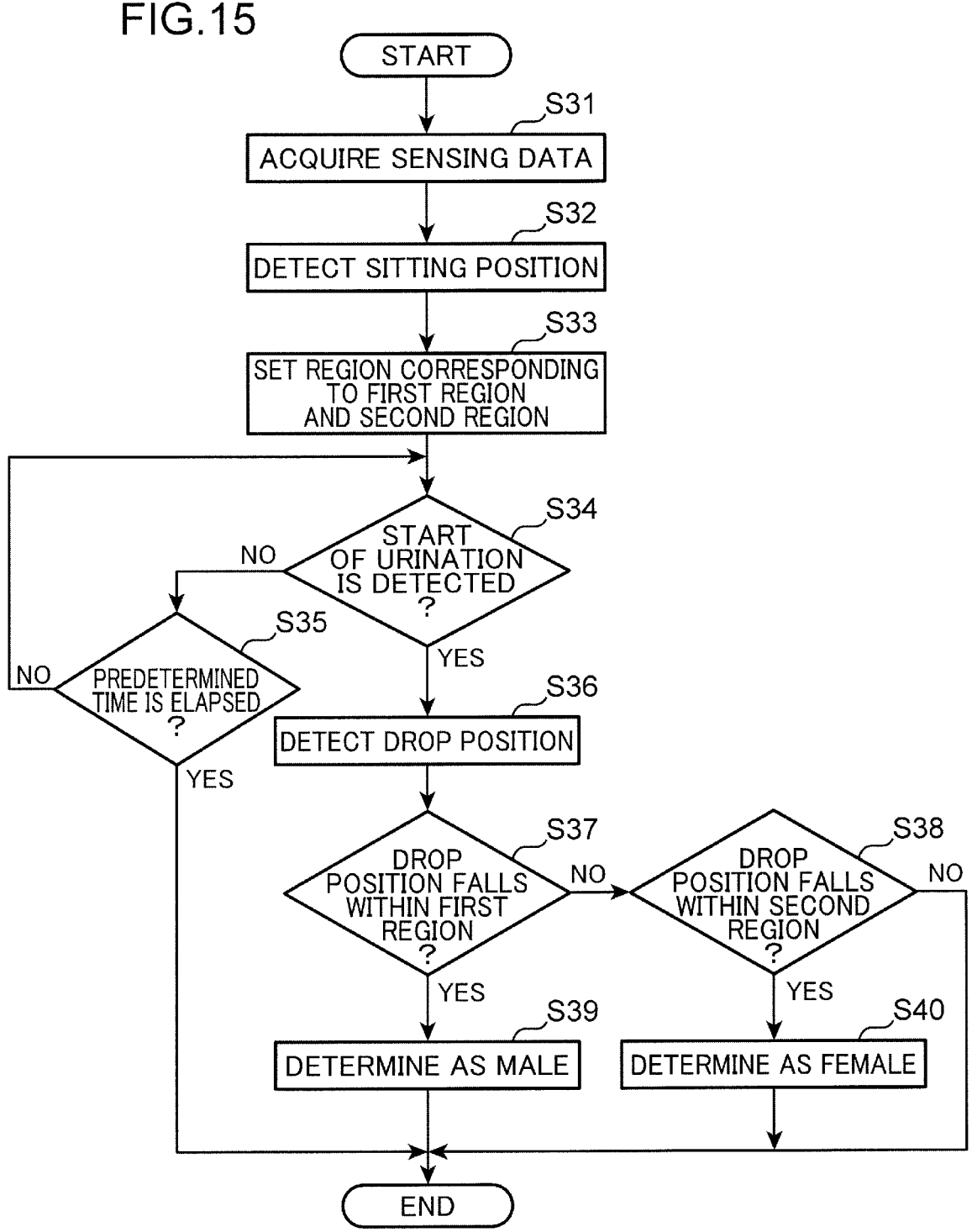
FIG. 15 is a flowchart showing an example of a process by the image capturing device according to the second embodiment of the disclosure.

FIG. 15 is a flowchart showing an example of a process by the image capturing device 1A according to the second embodiment of the disclosure. It is noted here that the image capturing sensor 21 captures image data at a predetermined frame rate in parallel with the sequence in the flowchart in FIG. 15. In step S31, the gender determination part 314 acquires sensing data for a determination of a sitting position. Here, image data captured by the image capturing sensor 21 is adopted as sensing data.

Figure 16:
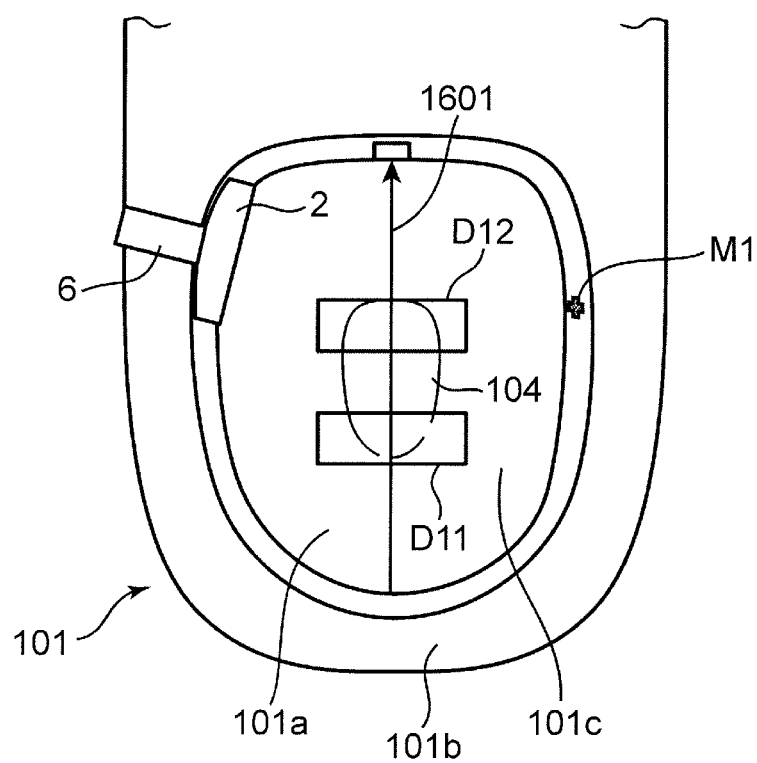
FIG. 16 is an explanatory view of the process by the image capturing device according to the second embodiment.

In step S32, the gender determination part 314 detects a sitting position of an excreter from the sensing data. FIG. 16 is an explanatory view of a process by the image capturing device 1A according to the second embodiment. The sitting position is represented with use of a coordinate axis 1601 shown in FIG. 16. The coordinate axis 1601 includes, for example, a one-dimensional coordinate in a longitudinal direction agreeing with the front-rear direction.

In use of the image data as the sensing data, the sitting position is detectable by the following three ways. The first way includes detecting the sitting position based on the top of buttocks seen on the image data. For instance, the gender determination part 314 performs image processing based on the image data acquired when the excreter sits on a toilet seat 102, and detects a position of the top of the buttocks thereof on the image data. For example, the gender determination part 314 may extract, based on a ratio of RGB color components, a region representing the buttocks from the image data, and detect a lower end on a contour line of the extracted region as the top of the buttocks. Then, the gender determination part 314 may calculate a position corresponding to the position of the top of the buttocks on the coordinate axis 1601, and detects the calculated position as the sitting position.

The second way includes detecting the anus of the excreter from the image data, and detecting, based on the position of the detected anus, the sitting position. For example, the gender determination part 314 may detect, based on a starting point of stool during excretion, a position of the anus from image data about the excretion. The gender determination part 314 may extract a region of the stool in the excretion from the image data, and detect a position at an upper end of the extracted region of the stool as the starting point of the stool. Then, the gender determination part 314 may calculate a position corresponding to the detected position of the anus on the coordinate axis 1601, and detect the calculated position as the sitting position.

The third way includes detecting, based on brightness of the image data, the sitting position. When the excreter sits on the edge of the toilet seat 102, a large amount of light enters into the bowl from outside. Thus, image data captured by the image capturing sensor 21 is brighter. Contrarily, when the excreter sits back on the toilet seat 102, the amount of the light entering into the bowl from the outside is smaller. Thus, image data captured by the image capturing sensor 21 is darker. In other words, the sitting position and the brightness in the bowl 101a correlate with each other. The third way of detecting the sitting position is established by using the correlation.

For instance, the gender determination part 314 obtains luminance of the image data acquired when the excreter sits on the toilet seat 102. For example, the gender determination part 314 may calculate an average value of the luminance of a plurality of pixels constituting the image data as the luminance of the image data. The luminance of each pixel can take, for example, an average value of each value of R, G, B in each pixel. Then, the gender determination part 314 may calculate, as the sitting position of the excreter, a sitting position corresponding to the calculated luminance of the image data with reference to a table preliminarily associating luminance of image data with each sitting position.

Alternatively, an illuminance sensor may be used to detect the sitting position. As described above in relation to the third way, the sitting position and the brightness in the bowl 101a correlate with each other. In this regard, the gender determination part 314 may specify a sitting position corresponding to an illuminance in the bowl 101a as detected by the illuminance sensor with reference to a table preliminarily associating an illuminance in the bowl 101a with each sitting position, and detect the specified sitting position as the sitting position of the excreter. In this case, the illuminance sensor may be provided in the housing 24 of a sensor unit 2. Besides, in this case, data indicating the illuminance detected by the illuminance sensor is adopted as sensing data.

In step S33, the gender determination part 314 sets, based on the detected sitting position, a region corresponding to each of the first region and the second region on the image data. FIG. 16 shows a first region D11 and a second region D12. The first region D11 is a predetermined rectangular region on a plane of the bowl 101a that is presumed to receive dropping urine in urination by a male. The second region D12 is a predetermined rectangular region on the plane of the bowl 101a that is presumed to receive dropping urine in urination by a female. A drop position of urine for the male is in front of that for the female. Thus, the first region D11 is set in front of the second region D12. Each of the first region D11 and the second region D12 is symmetric across the center line of an opening section 101c in a top view of the bowl 101a. The shape of each of the first region D11 and the second region D12 is not limited to the rectangular shape, but may be a circular shape.

Each of the first region D11 and the second region D12 is not fixed in view of a possibility of deviation of a drop position of urine from the first region D11 and the second region D12 depending on the sitting position of the excreter. Taking this into consideration, in the embodiment, each of the first region D11 and the second region D12 is set to a predetermined position depending on a sitting position. For instance, each of the first region D11 and the second region D12 is shiftable frontward in accordance with frontward shifting of the sitting position.

The region set on the image data to correspond to each of the first region D11 and the second region D12 has a predetermined size and shape based on the respective size and shape of the first region D11 and the second region D12 presumed when the first region D11 and the second region D12 are projected onto an imaging capturing plane of the image capturing sensor 21.

In step S34, the gender determination part 314 determines whether urination is started. The gender determination part 314 may determine that the urination is started when detecting a parabolically changing object from specific image data by monitoring a plurality of pieces of image data captured by the image capturing sensor 21.

When the start of the urination is detected (YES in step S34), the gender determination part 314 detects a drop position of urine (step S36). The gender determination part 314 may determine, as the drop position, a lower end of the parabolically changing object by monitoring the pieces of image data captured by the image capturing sensor 21.

Contrarily, when the start of urination is not detected (NO in step S34), the gender determination part 314 determines whether a predetermined time elapses (step S35). When the predetermined time elapses (YES in step S35), it is determined that no excretion occurred by the excreter, and then the process is finished. Contrarily, when the predetermined time does not elapse (NO in step S35), the process returns to step S34.

In step S37, the gender determination part 314 determines whether the drop position falls within the first region D11 (step S37). When it is determined that the drop position falls within the first region D11 (YES in step S37), the gender determination part 314 determines that the excreter is a male (step S39). In contrast, when the drop position does not fall within the first region D11 (NO in step S37), the gender determination part 314 determines whether the drop position falls within the second region D12 (step S38). When it is determined that the drop position falls within the second region D12 (YES in step S38), the gender determination part 314 determines that the excreter is a female (step S40). Contrarily, when it is determined that the drop position does not fall within the second region D12 (NO in step S38), the gender determination part 314 finishes the process.

As described heretofore, the image capturing device 1A according to the second embodiment achieves a determination on a gender of an excreter by detecting a drop position of urine from image data.

Third Embodiment

In the first embodiment, the view angle and the attachment position of the sensor unit 2 are set so that the intersection P1 and the intersection P2 fall within the view field of the sensor unit 2 as shown in FIG. 2 to FIG. 5. In the third embodiment, a view angle and an attachment position of a sensor unit 2 are set, under the restriction that a detection area D1 shown in FIG. 13 falls within a view field of a sensor unit 2, so that a boundary L1 shown in FIG. 2 passes through a position P5 on a center line LC between an intersection P1 and an intersection P3 and that a boundary L2 passes through a position P6 on the center line LC between an intersection P4 and an intersection P2.

Conclusively, in the third embodiment, the view angle and the attachment position of the sensor unit 2 are set, under the restriction that the detection area falls within the view field of the sensor unit 2, so that the boundary L1 passes through the position P5 and that the boundary L2 passes through the position P6. Consequently, the smaller view angle allows the detection area D1 to fall within the view field.

INDUSTRIAL APPLICABILITY

This disclosure permits excrement to fall within a view angle, and therefore, is useful in the technical field for detecting, based on image data, excrement.

The invention claimed is:

1. An image capturing device that captures an image of excrement, comprising:
   a sensor unit attached to a fringe part of a toilet having a bowl, the fringe part being located at a top of the bowl, the sensor unit including an image capturing sensor, wherein
   a view angle and an attachment position of the sensor unit are set so that a detection area presumed to receive dropping excrement in the bowl falls within a view field of the sensor unit, wherein
   the fringe part defines an opening section,
   a center line of the opening section extending in a front-rear direction bears, in a top view of the opening section,
   a first position being a predetermined position between a first intersection of a front intersection of the center line and the opening section and a second intersection of a front intersection of the center line and the detection area, and
   a second position being a predetermined position between a third intersection of a rear intersection of the center line and the detection area and a fourth intersection of a rear intersection of the center line and the opening section, and
   the view angle and the attachment position of the sensor unit are set so that the first position and the second position fall within the view field.

2. The image capturing device according to claim 1, wherein
   the first position is at the first intersection, and
   the second position is at the fourth intersection.

3. The image capturing device according to claim 1, wherein
   the attachment position is to the rear of the detection area, at an inflection point of the contour of the opening area, and
   the view angle is 83 degrees or more.

4. The image capturing device according to claim 1, wherein
   the attachment position is in front or in the rear of the detection area, and
   the view angle is 101 degrees or more.

5. The image capturing device according to claim 1, wherein
   the view angle is 105 degrees or more.

6. The image capturing device according to claim 1, further comprising an attachment part for removably attaching the sensor unit to the toilet.

7. The image capturing device according to claim 1, further comprising a calibration execution part that
   acquires, from the image capturing sensor, image data containing an image of a mark provided at a specific position of the toilet,
   detects a position of the mark from the acquired image data, and
   calibrates setting of an area corresponding to the detection area to the image data based on the detected position.

8. The image capturing device according to claim 1, further comprising a gender determination part that
   detects a drop position of urine in the bowl from the image data captured by the image capturing sensor, and
   determines, based on the detected drop position, a gender of an excreter.

9. The image capturing device according to claim 8, wherein the gender determination part determines that the excreter is a male when the drop position falls within a first region, and determines that the excreter is a female when the drop position falls within a second region in the rear of the first region.

10. The image capturing device according to claim 9, wherein the gender determination part detects a sitting position of the excreter, and changes, based on a determination result of the gender determination part, the first region and the second region.

* * * * *